United States Patent
Lu

(10) Patent No.: US 8,647,384 B2
(45) Date of Patent: Feb. 11, 2014

(54) ACCOMMODATING INTRAOCULAR LENS

(76) Inventor: Kenneth L. Lu, Arcadia, CA (US)

( * ) Notice: Subject to any disclaimer, the term of this patent is extended or adjusted under 35 U.S.C. 154(b) by 332 days.

(21) Appl. No.: 12/943,376

(22) Filed: Nov. 10, 2010

(65) Prior Publication Data

US 2012/0078363 A1  Mar. 29, 2012

Related U.S. Application Data

(60) Provisional application No. 61/262,082, filed on Nov. 17, 2009.

(51) Int. Cl.
*A61F 2/16* (2006.01)

(52) U.S. Cl.
USPC .......... 623/6.43; 623/6.37; 623/4.1; 623/6.46

(58) Field of Classification Search
USPC ............................................... 623/6.37–6.55
See application file for complete search history.

(56) References Cited

U.S. PATENT DOCUMENTS

| | | | |
|---|---|---|---|
| 5,628,795 A * | 5/1997 | Langerman | 623/4.1 |
| 6,413,277 B1 * | 7/2002 | Neuhann | 623/6.39 |
| 6,428,572 B2 * | 8/2002 | Nagai | 623/4.1 |
| 6,558,419 B1 * | 5/2003 | Pham et al. | 623/6.16 |
| 2003/0171808 A1 * | 9/2003 | Phillips | 623/6.37 |
| 2006/0047339 A1 * | 3/2006 | Brown | 623/6.13 |
| 2006/0116765 A1 * | 6/2006 | Blake et al. | 623/6.46 |

* cited by examiner

*Primary Examiner* — David H Willse
*Assistant Examiner* — Tiffany Shipmon
(74) *Attorney, Agent, or Firm* — James A. Italia; Italia IP

(57) ABSTRACT

An accommodating intraocular lens includes an adjustable optic, wherein the optic is capable of being moved between an accommodated state and an unaccommodated state. The optic includes an anterior portion, a posterior portion, and a sidewall between the anterior portion and the posterior portion. The lens further includes a ring disposed about the optic sidewall and a haptic coupled to the ring. The haptic is capable of being coupled to a patient's capsular bag. A method for implanting an accommodating intraocular lens is also provided.

2 Claims, 14 Drawing Sheets

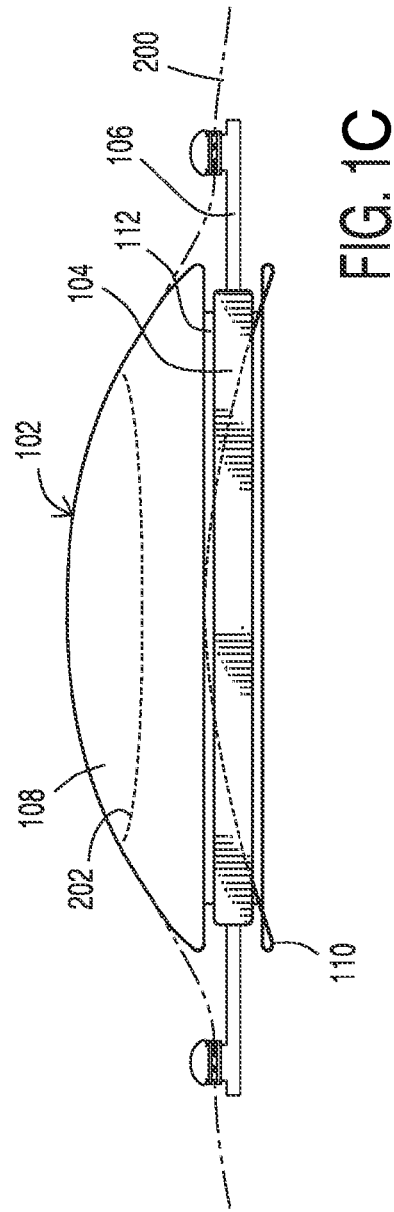
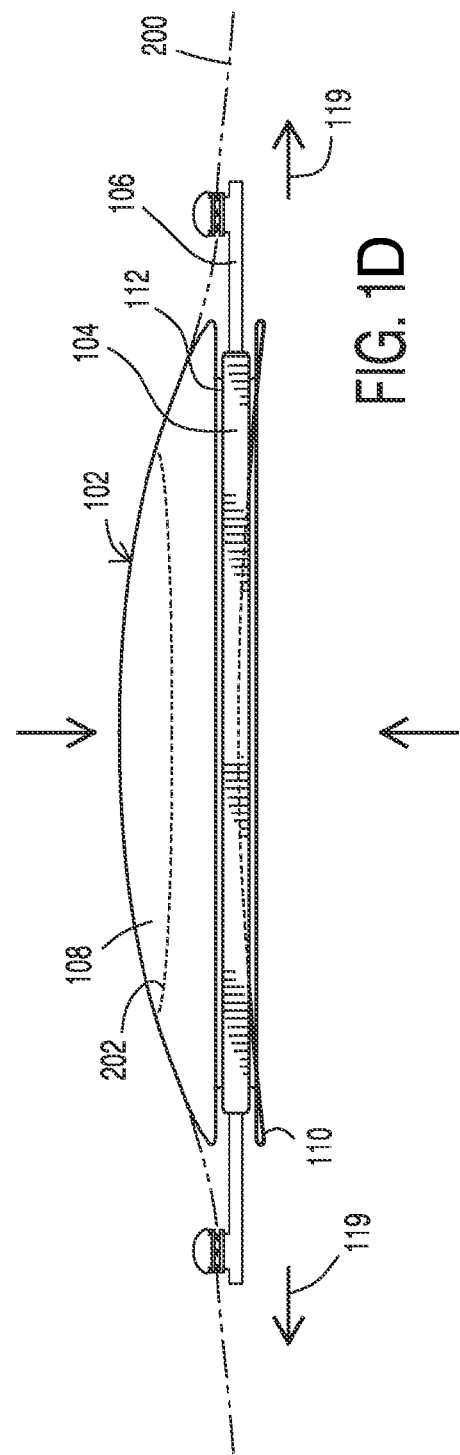

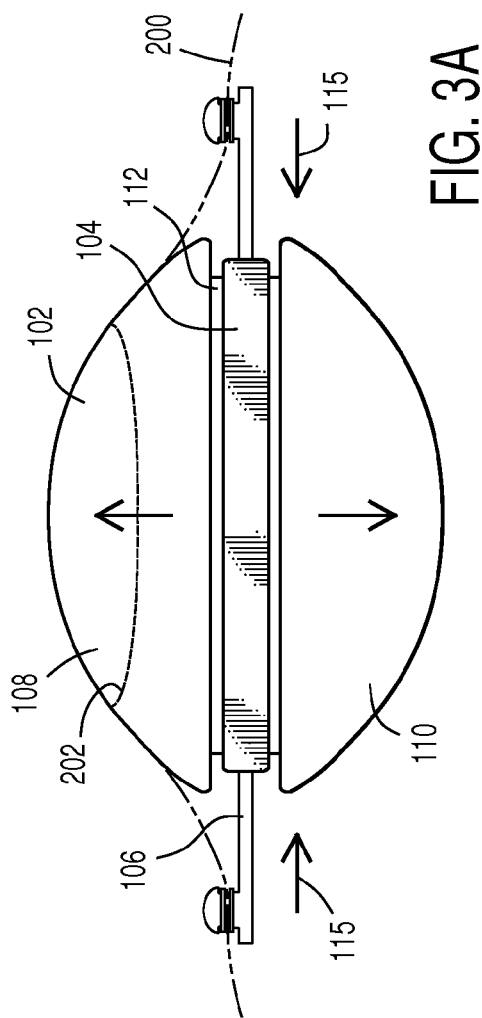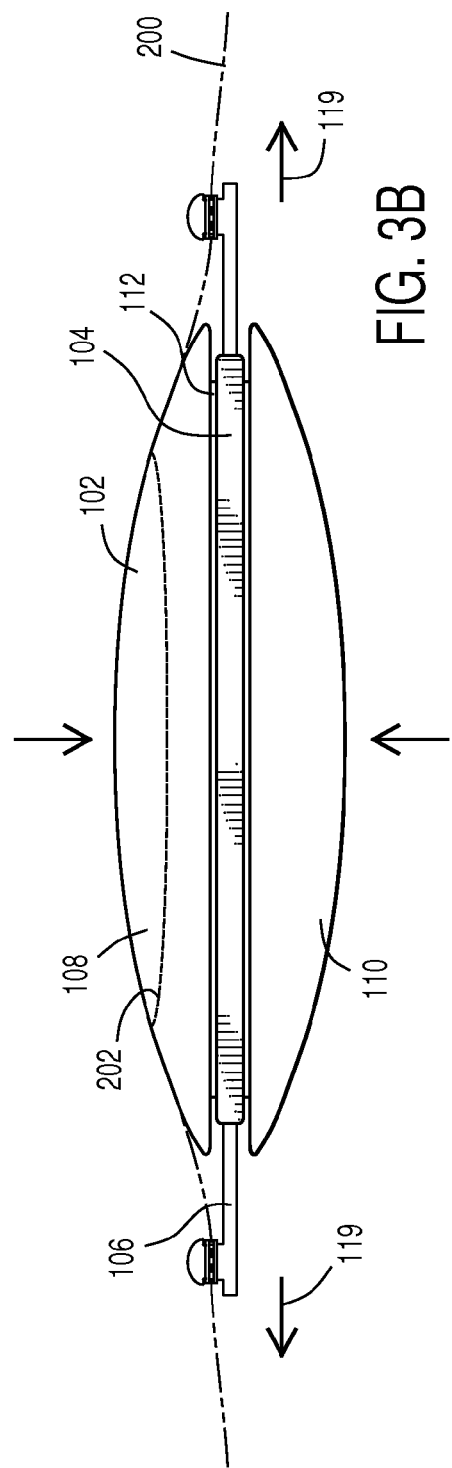

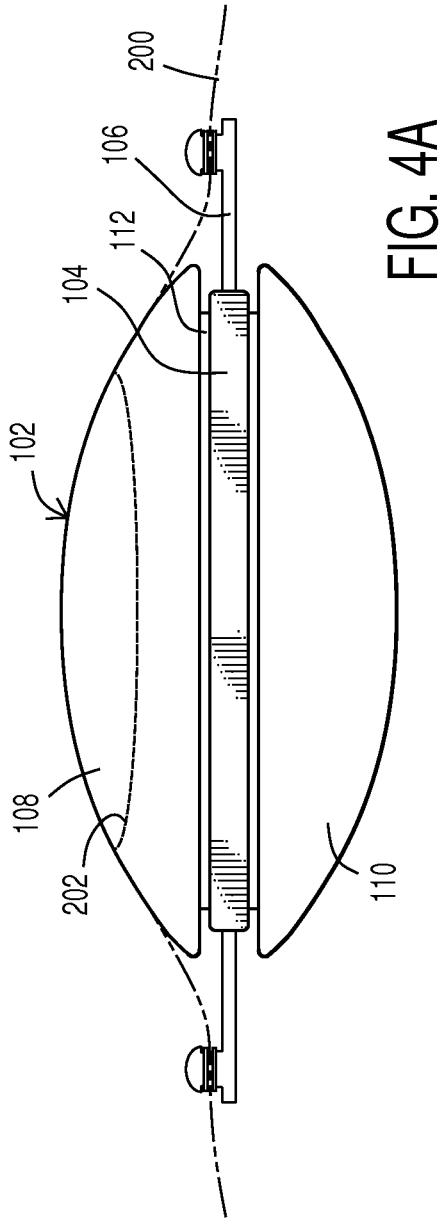
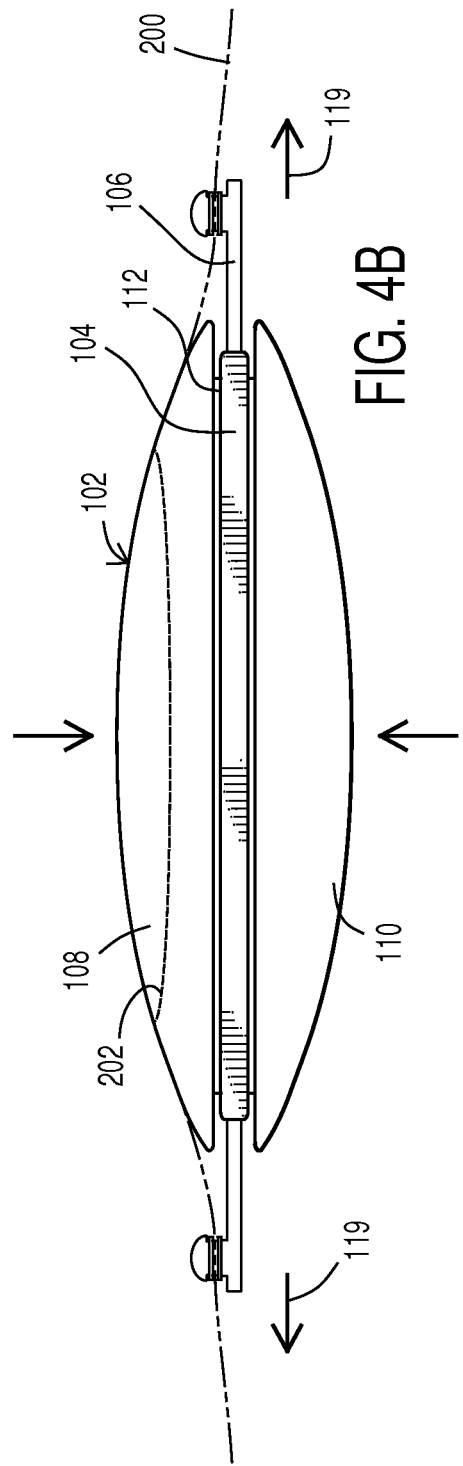

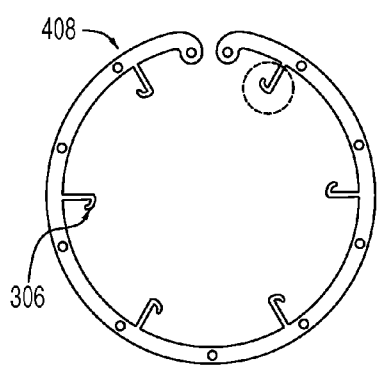
FIG. 16
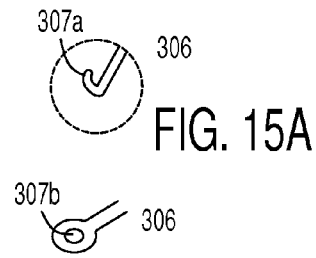
FIG. 15A
FIG. 15B
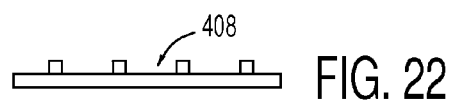
FIG. 22
FIG. 23
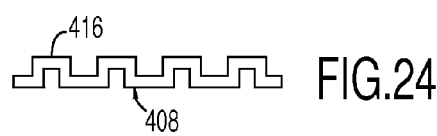
FIG. 24
FIG. 25
FIG. 26
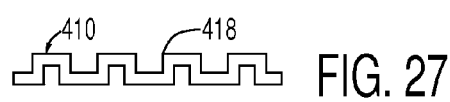
FIG. 27
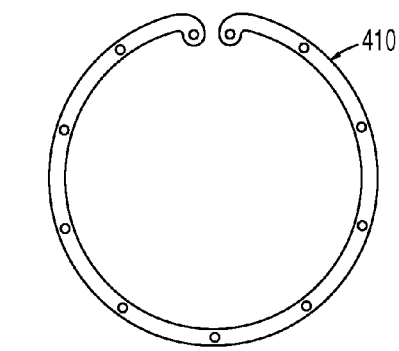
FIG. 17
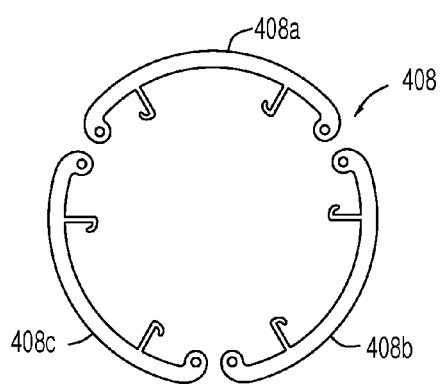
FIG. 20
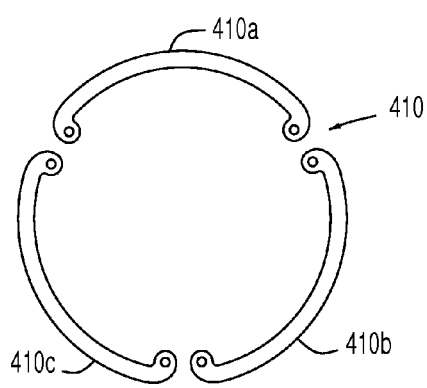
FIG. 21

ACCOMMODATING INTRAOCULAR LENS

CROSS REFERENCE TO RELATED APPLICATION

This application claims the benefit of the filing date under 35 USC 119(e) of the filing date of U.S. Provisional Application Ser. No. 61/262,082, filed Nov. 17, 2009.

FIELD OF THE INVENTION

The present invention relates to intraocular lenses and more particularly to accommodating intraocular lenses.

BACKGROUND AND SUMMARY

In an eye, accommodation is a process whereby the eye adjusts focus from far to near to allow for clear viewing at multiple distances. Accommodation involves the ciliary muscle or body, zonules, capsular bag and the crystalline lens. The ciliary muscle is a circumferential sphincter muscle that lines the inside of the eye and adjacent to the eye wall. When the ciliary muscle contracts, it moves inward towards the center of the eye and when the ciliary muscle relaxes it moves outward towards the eye wall.

The ciliary muscle is connected to zonules. Zonules are attachment ligaments that attach to the ciliary muscle peripherally, and to the periphery of the capsular bag which encompasses the crystalline lens, centrally. Thus, the ciliary muscle, zonules and crystalline lens are connected, and movement of one causes movement of the others.

The crystalline lens is a disc-shaped viewing and refracting component of the eye. The lens is enveloped by the capsular bag. The lens and capsular bag are highly elastic and change shape with external compressive or deforming forces. The natural resting shape of the crystalline lens is a rounded disc shape. This shape, known as the accommodated state, has higher refractive power and provides clear viewing of nearer objects. The lens may be pulled centrifugally, via the zonules, by the ciliary muscle into a sagittally flatter shape, i.e., the unaccommodated state. The flatter shape has lower refractive power and provides clear viewing of more distant objects. Incremental changes in between the two shapes provides for smooth transition between distance and near viewing. When the ciliary muscle is in a relaxed state, the crystalline lens is pulled into its flatter shape for distance viewing. When the ciliary muscle contracts, the crystalline lens is allowed to relax into its more rounded shape for near viewing.

Presbyopia, or loss of accommodating ability with age, develops due to several factors. The crystalline lens loses elasticity with age, thereby losing the ability to resume the more rounded shape with age. While ciliary muscle continues to contract, the lens no longer responds as it once did. Also, there is recent evidence from high resolution MRI studies indicating that the ciliary muscle circumference may decrease with age, while the crystalline lens equatorial circumference remains fairly stable in adulthood. This causes a decrease in the distance between ciliary muscle and equator of lens and a concomitant decrease in zonular tension. Thus, with age when the ciliary muscle contracts and relaxes, its force is not as effectively transferred to the lens due to the laxity in the zonules.

Cataract, or the clouding of the crystalline lens, may also adversely affect vision. Cataract causes obstruction and a decrease of vision. The current form of treatment of a cataract is the removal of the cataract and implantation of an artificial intraocular lens. Artificial intraocular lenses typically come in three forms: monofocal; multifocal; and accommodating.

The monofocal lenses have a single refractive power providing the patient with clear, unaided vision at one particular viewing distance; however, refractive correction is required for viewing at other distances. Multifocal lenses are one attempt at providing clear vision at multiple distances. Multifocal lenses sometimes result in undesirable side effects, such as dim light glare, halos and loss of contrast sensitivity. Accommodating lenses are another attempt at providing clear vision at multiple distances. While accommodating lenses do not typically have the side effects of multifocal lenses, most accommodating lenses have not been very effective. Therefore, there exists a significant need for an improved accommodating intraocular lens.

In particular, this application discloses an intraocular lens comprising: an adjustable optic, the optic capable of being moved between an accommodated state and an unaccommodated state, the optic comprising: an anterior portion; a posterior portion; a sidewall between the anterior portion and the posterior portion; a ring disposed about the optic sidewall; and a haptic coupled to the ring, the haptic capable of being coupled to a patient's capsular bag.

This application also discloses an eyelet for coupling an intraocular lens to a capsular bag of a patient, the eyelet comprising: a first portion comprising: an annular body; a lip disposed about a first end of the first portion annular body, the lip operable to abut an exterior surface of the capsular bag; a second portion comprising: an annular body; a lip disposed about a first end of the second portion annular body, the lip operable to abut an interior surface of the capsular bag; wherein at least one of the first portion and second portion is configured to lockingly engage the other one of the first portion and second portion when at least a portion of the capuslar bag is disposed between the first portion and second portion.

This application further discloses a method for implanting an intraocular lens in a capsular bag of a patient's eye from which the natural lens has been removed, the method comprising: installing an intraocular lens within the capsular bag, the intraocular lens comprising: an adjustable optic, the optic capable of being moved between an accommodated state and an unaccommodated state, the optic comprising: an anterior portion; a posterior portion; a sidewall between the anterior portion and the posterior portion; a ring disposed about the optic sidewall; and haptic coupled to the ring; installing an eyelet in the capsular bag; stretching the intraocular lens; and coupling the lens haptic to the eyelet.

BRIEF DESCRIPTION OF THE DRAWINGS

The drawings, when considered in connection with the following description, are presented for the purpose of facilitating an understanding of the subject matter sought to be protected.

FIG. 1C is a side environmental view of an alternative accommodating intraocular lens in an accommodated state;

FIG. 1D is a side environmental view of the accommodating intraocular lens of FIG. 1C in an unaccommodated state;

FIG. 3A is a side environmental view of the illustrative accommodating intraocular lens of FIG. 1A in an accommodated state;

FIG. 3B is a side environmental view of the illustrative accommodating intraocular lens of FIG. 3A in an unaccommodated state;

FIG. 4A is a side environmental view of an alternative accommodating intraocular lens in an accommodated state;

FIG. 4B is a side environmental view of the accommodating intraocular lens of FIG. 4A in an unaccommodated state;

FIG. 15A is side view of a haptic;

FIG. 15B is a side view of an alternative haptic;

FIG. 16 is a top view of an endocapsular portion of the ring scaffold;

FIG. 17 is a top view of an extracapsular portion of the ring scaffold;

FIG. 20 is a top view of an endocapsular portion of the ring scaffold having a plurality of segments;

FIG. 21 is a top view of an extracapsular portion of the ring scaffold having a plurality of segments;

FIG. 22 is a side view of an endocapsular portion of the ring scaffold;

FIG. 23 is a side view of an alternative endocapsular portion of the ring scaffold;

FIG. 24 is a side view of an alternative endocapsular portion of the ring scaffold;

FIG. 25 is a side view of an extracapsular portion of the ring scaffold;

FIG. 26 is a side view of an alternative extracapsular portion of the ring scaffold;

FIG. 27 is a side view of an alternative extracapsular portion of the ring scaffold;

DETAILED DESCRIPTION

Figure 1A:
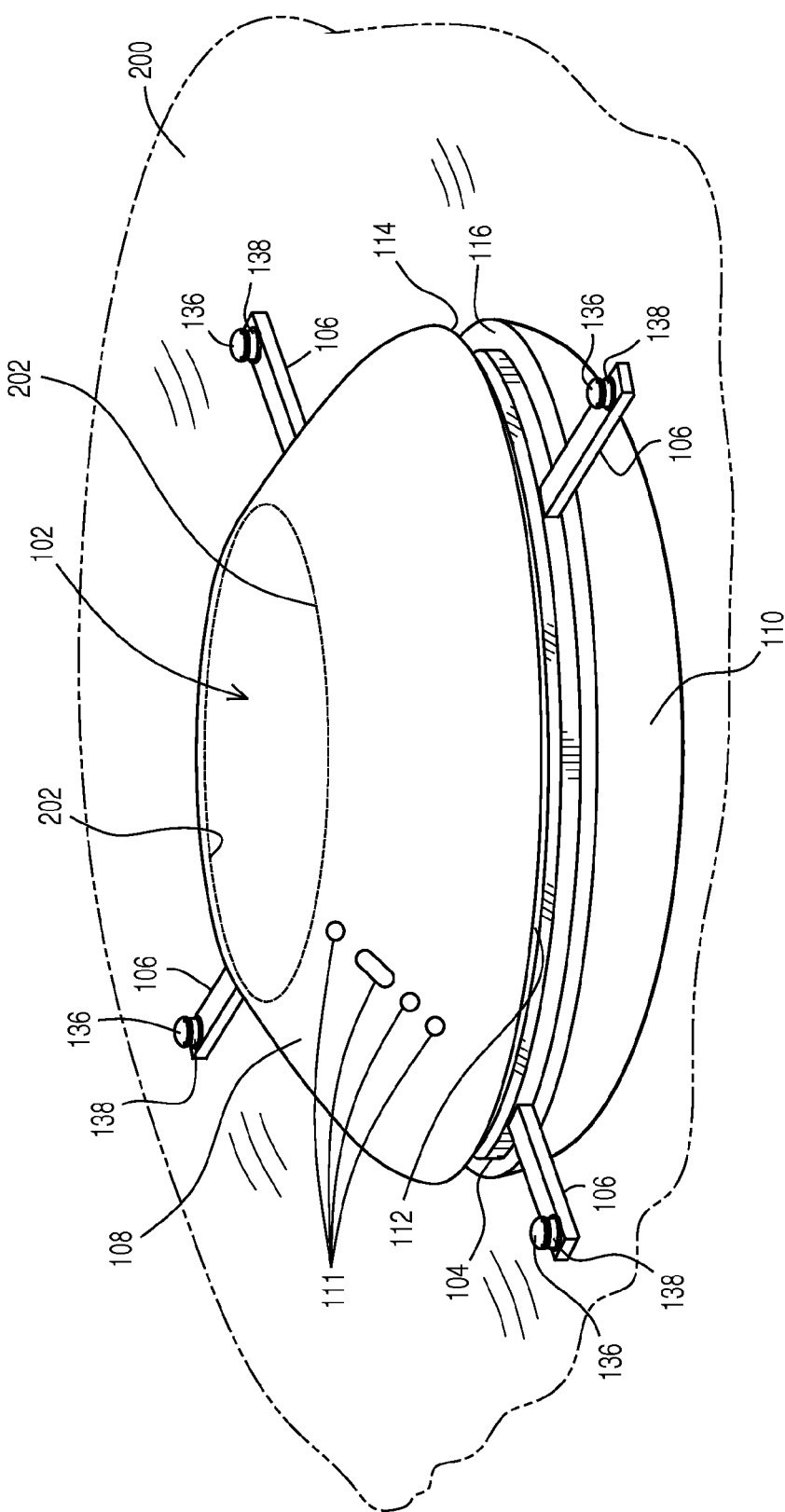
FIG. 1A is an environmental view of an illustrative accommodating intraocular lens.
Figure 1B:
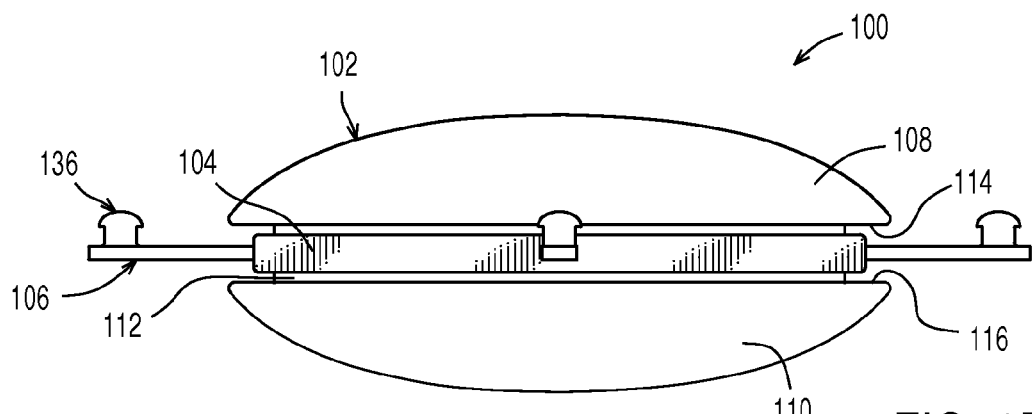
FIG. 1B is a side view of the illustrative accommodating intraocular lens of FIG. 1A.

Referring now to the FIGS., wherein like numerals indicate like elements throughout, an illustrative intraocular lens 100 is shown. With particular reference to FIGS. 1A and 1B, the intraocular lens 100 includes an adjustable optic 102, an elastic ring 104, and one or more haptics 106. The optic 102 includes an anterior portion 108 and a posterior portion 110. A sidewall 112 separates the anterior portion 108 and posterior portion 110.

As best shown in FIG. 1B, the anterior portion 108 may have a diameter larger than the diameter of the sidewall 112 such that the anterior portion 108 extends beyond the sidewall 112, wherein a ledge 114 defined thereby may prevent the ring 104 from sliding off of the sidewall 112. Also, the posterior portion 110 may have a diameter larger than the diameter of the sidewall 112 such that the posterior portion 110 extends beyond the sidewall 112, wherein a ledge 116 defined thereby may prevent the ring 104 from sliding off of the sidewall 112. In one embodiment, the intersection of the posterior portion 110 and ledge 116 may be squared to prevent posterior capsular opacity.

Figure 2A:
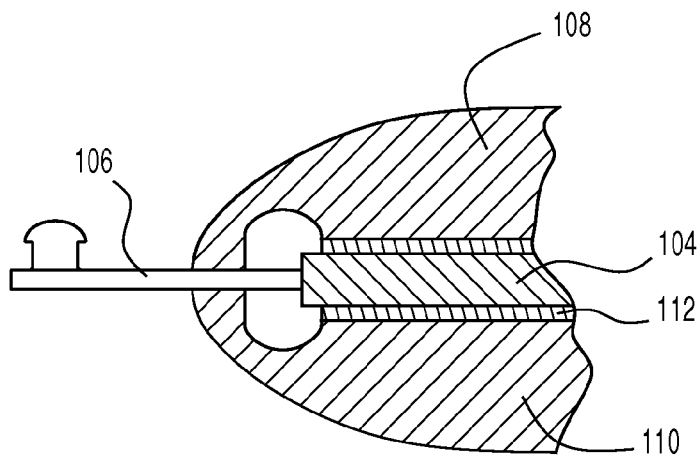
FIG. 2A is a cross-sectional, partial side view of an alternative accommodating intraocular lens.
Figure 2B:
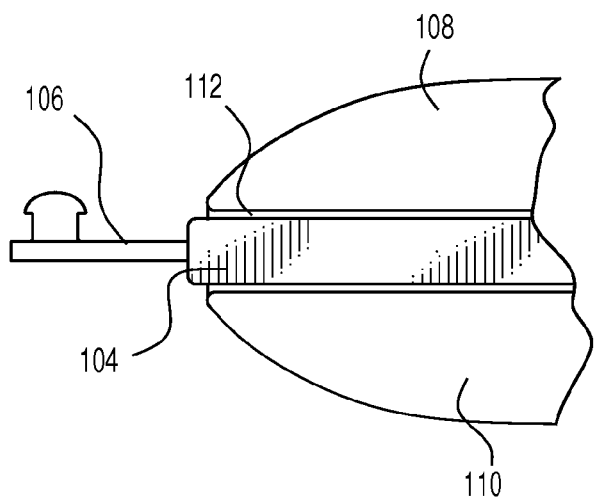
FIG. 2B is a partial side view of an alternative accommodating intraocular lens.

In an alternative embodiment, as best shown in FIG. 2A, at least one of the anterior portion 108 and posterior portion 110 may overlap the sidewall 112 such that the sidewall 112 may be encompassed by the overlapping portion(s) of the anterior portion 108 and/or posterior portion 110 whereby the haptic(s) 106 extend from the ring 104 and through, or between, the overlapping portion(s) of the anterior portion 108 and/or posterior portion 110. In yet another alternative, as best shown in FIG. 2B, one or both of the anterior portion 108 and posterior portion 110 may terminate at the sidewall 112 such that the sidewall 112 is substantially flush with the edge(s) of one or both of the anterior portion 108 and posterior portion 110.

Referring again to FIGS. 1A and 1B, in the illustrative embodiment, the anterior portion 108 and posterior portion 110 both have generally convex configurations. However, it will be appreciated that each of the anterior portion 108 and posterior portion 110 may have any suitable configuration, including, but not limited to, substantially concave, substantially planar, etc. For example, and without limitation, as shown in FIGS. 1C and 1D, an optic 102 having a convex anterior portion 108 and a concave posterior portion 110 is shown in both an accommodated state (FIG. 1C) and an unaccommodated state (FIG. 1D). Additionally, the anterior portion 108 and/or posterior portion 110 may have different radius of curvatures and/or radius of curvatures along different meridians such that the optic 102 may be capable of correcting astigmatism. The anterior portion 108 and/or posterior portion 110 may include markings 111, such as lines, raised dots, or the like, to assist in proper optic 102 orientations in the patient's eye during implantation.

The optic 102 may be moved between an accommodated state, for near vision, and an unaccommodated state, for distance vision. As will be discussed further below, the optic 102 is coupled to the patient's capsular bag 200, via the ring 104, such that the optic 102 may be moved between the accommodated state with contraction of the patient's ciliary muscle, and the unaccommodated state with relaxation of the patient's ciliary muscle. In one embodiment, as shown in FIGS. 3A and 3B, the ring 104 is disposed about the sidewall 112 and operable to bias the optic 102 in an accommodated state (FIG. 3A). The ring 104 is an elastic ring and operable to provide a compressive force, as represented by force vectors 115, such that the anterior portion 108 and/or posterior portion 110 are forced to a thicker and/or more rounded configuration, i.e. the accommodated state where the optic 102 has a higher refractive power for near viewing. In one embodiment, the AIOL is stretched to attach to the capsule and may be capable of increasing the tension in the patient's zonules. Further, as best shown in FIG. 3B, when the ciliary muscle begins to relax, i.e. expand its circumference, the compressive force created by the ring 104 begins to be overcome by the force generated by outward movement of the ciliary muscle, as represented by force vectors 119, and the optic 102 is stretched thinner and/or flatter, i.e. the unaccommodated state, where the optic has a lower refractive power for distance viewing. The ring 104 or the side wall 112 of the optic may be opaque to reduce internally reflected light and thereby symptoms of glare and halos.

In an alternative embodiment, as shown in FIGS. 4A and 4B, the optic 102 may naturally rest in the accommodated state (FIG. 4A). In this embodiment, the ring 104 does not bias the optic in the accommodated state but serves to transfer force generated by outward expansion of the patient's ciliary muscle, as represented by force vectors 119 in FIG. 4B, whereby the optic 102 is moved to the unaccommodated state.

When the optic 102 moves to an accommodated state, the radius curvature of at least one of the anterior portion 108 and posterior portion 110 may be decreased. In an alternative embodiment, the radius of curvature for both the anterior portion 108 and posterior portion 110 may decrease when the optic 102 is moved to an accommodated state. Also, in one embodiment, when the optic 102 moves to an unaccommodated state, the radius of curvature of at least one of the anterior portion 108 and posterior portion 110 may increase. Alternatively, the radius of curvature for both the anterior portion 108 and posterior portion 110 may increase when the optic 102 is moved to an unaccommodated state. Also, it will be appreciated that the radius of curvature for each the anterior portion 108 and posterior portion 100 may or may not be equal in the accommodated state and/or the unaccommodated state. Moreover, when the optic is moved to the accommodated state and/or unaccommodated state, it will be appreciated that the amount, or degree, of change in the radius of curvature of the anterior portion 108 may or may not be equal to amount or degree of change in the radius of curvature of the posterior portion 110.

The optic 102 may be formed from any suitable biocompatible material, including, but not limited to, acrylic, silicone, hydrogel, collamer, etc. Additives, such as UV or blue light absorptive chromophores, may also be included in the optic 102 material to block certain portions of the light spectrum from passing through the optic 102. The refractive power of the optic 102 at its resting state may be set during manufacturing using techniques known in the art. Moreover, as previously mentioned, in one embodiment, the optic 102 may be in an accommodated state at rest and configured to be moved towards the unaccommodated state as the ciliary muscle relaxes. In an alternative embodiment, as previously mentioned, the optic 102 may be in an unaccommodated state at rest and be biased to the accommodated state by the ring 104 wherein the optic 102 may be moved towards the unaccommodated state as the ciliary muscle relaxes and expands outwardly and force generated thereby overcomes the compressive force of the ring 104. With respect to the optic 102, the terms "rest", "rests" or "resting state," as used herein, refer to the natural state of the optic 102 without any outside forces acting thereon.

Figure 5A:
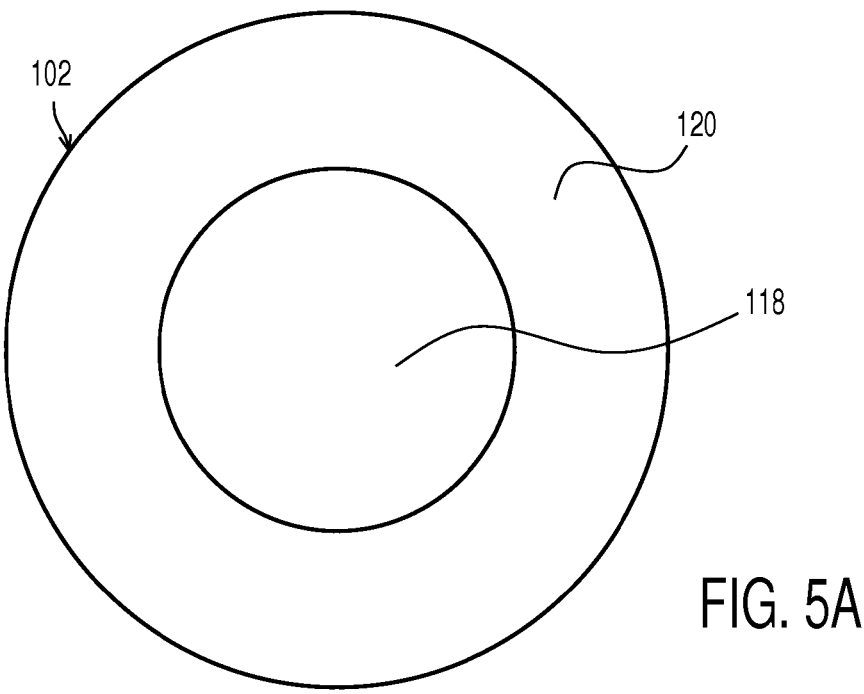
FIG. 5A is a top schematic view of an accommodating intraocular lens having zones with differing stiffnesses.
Figure 5B:
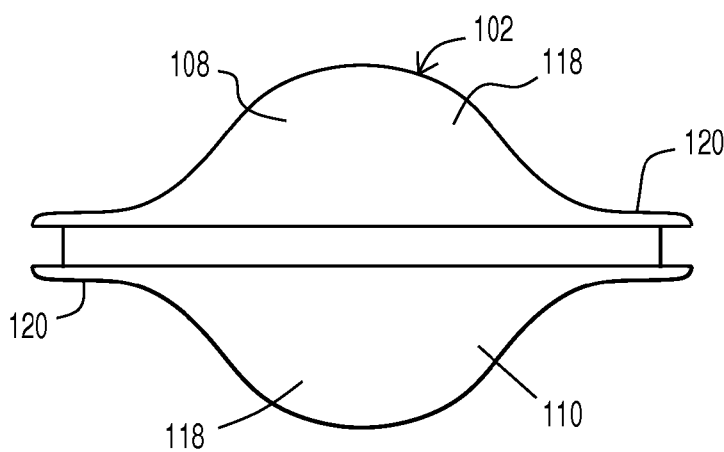
FIG. 5B is a side view of the accommodating intraocular lens of FIG. 5A in its accommodated state.
Figure 5C:
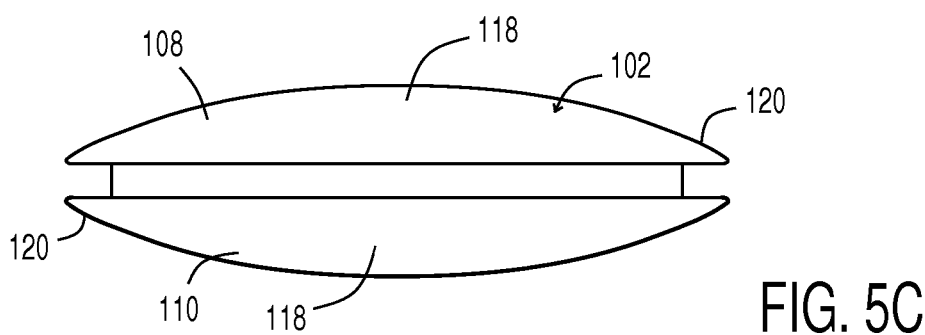
FIG. 5C is a side view of the accommodating intraocular lens of FIG. 5A in its unaccommodated state.

In one embodiment, as best shown in FIGS. 5A and 5B, the optic 102 may have different zones of elasticity whereby different zones of the optic 102 stretch or compress different amounts, or at different rates, under a load (e.g., from ciliary muscle contraction, ciliary muscle relaxation, elastic ring compression, etc.). In the illustrative embodiment, the optic 102 includes a peripheral zone 120 having a first modulus of elasticity and a central zone 118 having a second modulus of elasticity. In one embodiment, the first modulus of elasticity is greater than the second modulus of elasticity whereby the optic 102 deforms (e.g., compresses and/or stretches) a greater amount in the central zone 118 whilst under a load (see, e.g., FIG. 5B); however, when not under a load, there is no unequal deformation between the zones (see, e.g., FIG. 5C). Zones having different moduli of elasticity may be accomplished a variety of ways. In one embodiment, the zones may be formed from different polymers and/or include additional fillers or the like to provide a plurality of zones having different moduli of elasticity. Alternatively, reinforcements may be embedded in certain zones of the optic 102. For example, and without limitation, stiffening rings or radial elements may be embedded in some zones to increase zone stiffness. Alternatively, stiffening rings or radial elements may be coupled to the surface of one or more zones to increase zone stiffness. While the illustrative embodiment of FIGS. 5A and 5B, shows an optic 102 having two zones with different moduli of elasticity, it will be appreciated that any suitable number of such zones may be employed and remain within the scope of the present disclosure. Moreover, it will be appreciated that the anterior portion 108 and posterior portion 110 may be formed from different materials and/or have different stiffnesses relative to one another.

Figure 6:
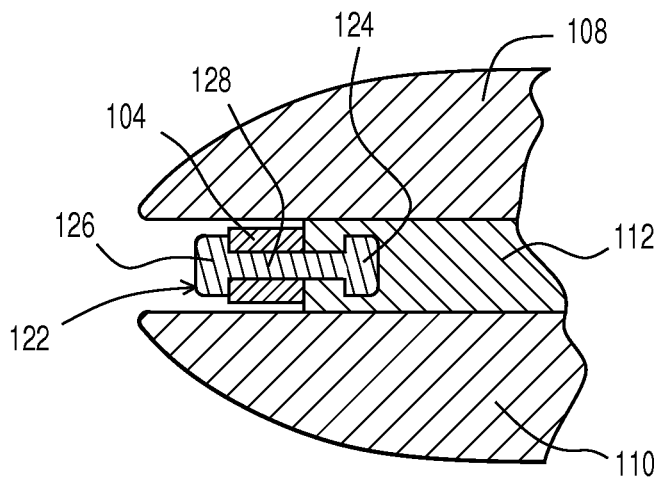
FIG. 6 is a cross-sectional, partial side view of the illustrative accommodating intraocular lens of FIG. 1A.

Referring again to FIGS. 1A and 1B, the ring 104 is disposed about the sidewall 112 of the optic 102. In one embodiment, the ring 104 and optic sidewall 112 are coupled via a friction fit. Alternatively, the ring 104 may be secured to the optic sidewall 112 via one or more fastener members 122. As best shown in FIG. 6, in the illustrative embodiment, each fastener member 122 includes a proximal head 124 and a distal head 126 interconnected by an intermediate portion 128. In the illustrative embodiment, the diameter of each head 124, 126 is greater than the diameter of the intermediate portion. The proximal head 124 is lockingly received within a corresponding aperture in, or otherwise embedded in, the optic sidewall 112. The intermediate portion 128 extends from the proximal head 124 and through the ring 104. The distal head 126 abuts the outer surface of the ring 104 whereby the ring 104 is secured between the heads 124, 126 and to the optic sidewall 112. Any suitable number of fastener members 122 may be employed to secure the ring 104 to the optic sidewall 112. While the illustrative embodiment employs fastener members 122 as shown in FIG. 6, it will be appreciated that the ring 104 may be secured to the sidewall 112 by any suitable means, including, but not limited to, adhesives, bonding, mechanical fasteners, sutures, etc.

Referring again to FIGS. 1A and 1B, the ring 104 is coupled to the patient's capsular bag 200, via any suitable implement or means as will be further discussed below, such that the force generated by the contraction or expansion of the patient's ciliary muscle may be imparted to the optic 102 whereby the optic 102 may move between an accommodated state and unaccommodated state as previously discussed. One or more haptics 106 may be coupled to the ring 104. Each haptic 106 extends from the ring 104 and is capable of being coupled to the patient's capsular bag 200 and is operable to translate forces from expansion and contraction of the ciliary muscle to the optic 102 via the ring 104.

Figure 7A:
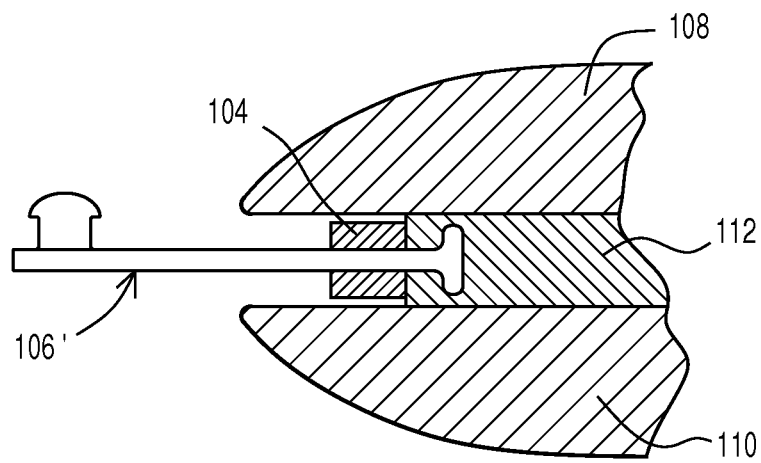
FIG. 7A is a cross-sectional, partial side view of an accommodating intraocular lens showing an attached haptic.
Figure 7B:
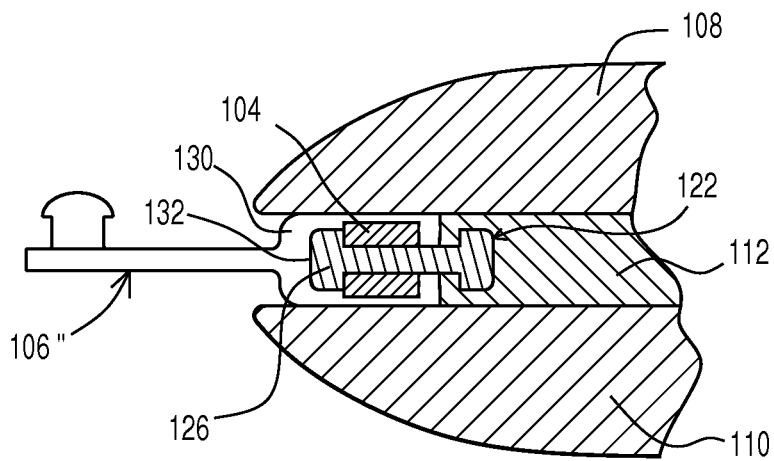
FIG. 7B is a cross-sectional, partial side view of an accommodating intraocular lens showing a movable haptic.

Referring now to FIGS. 7A and 7B, each haptic may be an attached haptic 106' (FIG. 7A) or a movable haptic 106" (FIG. 7B). The attached haptic 106' may be coupled to the ring 104 using any suitable means, including, but not limited to, adhesive, bonding, fasteners, etc. Alternatively, each attached haptic 106' may be integrally formed with the ring 104. In yet another alternative, as best shown in FIG. 7A, each attached haptic 106' may extend through the ring 104 and be lockingly received within, or otherwise embedded in, the optic sidewall 112.

Each movable haptic 106" is slidingly coupled to the ring 104 whereby each movable haptic 106" may moved to a permanent position on the ring 104 after the optic 102 has been placed within the patient capsular bag. In one embodiment, the proximal end 130 of the movable haptic 106" is configured to slidingly engage the ring 104 such that the haptic 106" may be moved about the ring 104. The distal head of the proximal end 130 may also include a notch 132 for engaging a distal head 126 of a fastener member 122 such that the movable haptic 106" may be lockingly secured to the ring 104 via engagement with the fastener member distal head 126 after being moved to the desired position on the ring 104. One or more fastener members 122 may be disposed about the ring 104 at desired positions for the movable haptics 106". While the distal end 130 is shown as a C-shaped end, it will be appreciated that the distal end 130 may have any suitable configuration for permitting the movable haptic 106" to slidingly engage the ring 104 until moved to the desired position whereafter the movable haptic 106" may be lockingly secured to the ring 104. While the illustrative embodiment employs the distal head 126 of a fastener member 122 to secure the movable haptics 106" to a desired position on the ring 104, it will be appreciated that the movable haptics 106" may be secured to a desired position on the ring 104 using any suitable means and remain within the scope of the present disclosure. For example, and without limitation, each movable haptic 106" may be secured to a desired position on the ring 104 with an adhesive, mechanical fastener, a friction fit, etc.

Figure 8A:
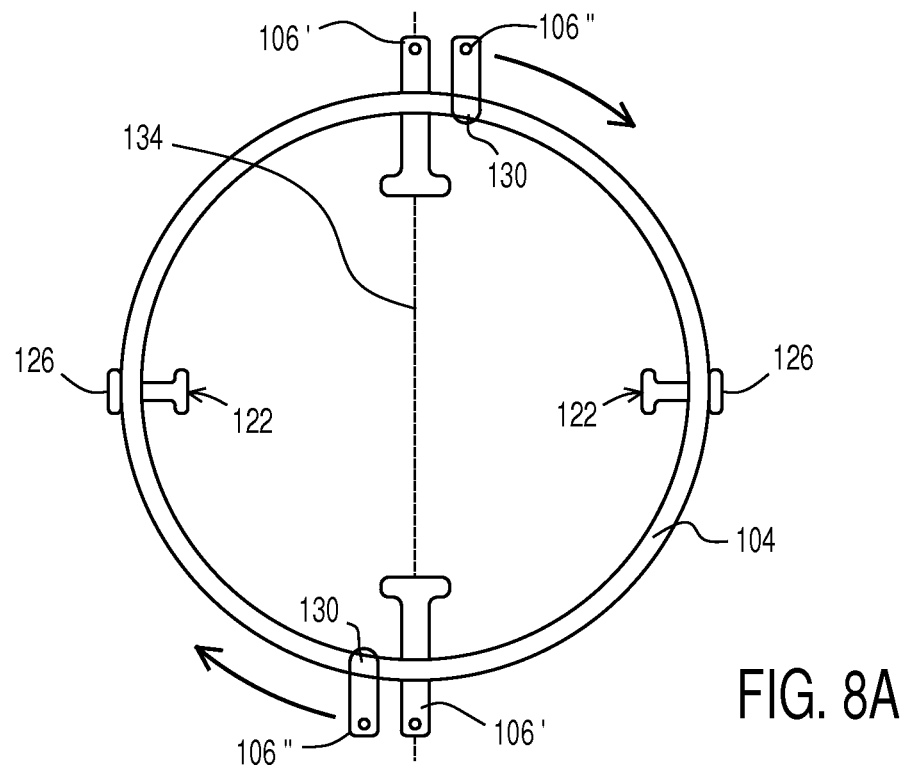
FIG. 8A is a top view of a ring having attached haptics and movable haptics coupled thereto.
Figure 8B:
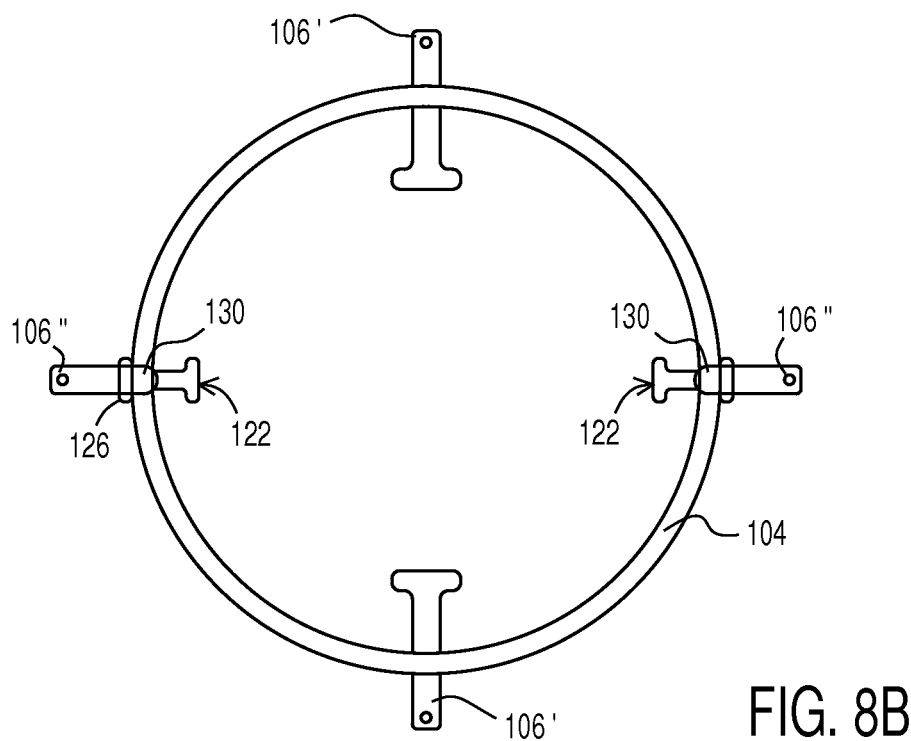
FIG. 8B shows the ring of FIG. 8A after the movable haptics have been moved to respective permanent positions.

Referring now to FIGS. 8A and 8B, a non-limiting, illustrative embodiment of a ring 104 having both attached haptics 106' and movable haptics 106" is shown. The attached haptics 106' are placed 180° opposite of each other about the ring 104. As shown in FIG. 8A, each of the movable haptics 106" may initially be disposed adjacent to a corresponding attached haptic 106'. The optic 102 may be folded along a line 134 substantially parallel with the attached haptics 106' to minimize the cross-sectional area of the optic 102 such that the optic 102 may be inserted through an incision in the eye as well as a hole 202 in the capsular bag 200. The movable haptics 106" may then be moved 90° to their respective permanent positions (as shown in FIG. 8B) whereby the notch in each proximal end 130 may lockingly engage the head 126 of a corresponding fastener member 122. While the illustrative embodiment shows a pair of attached haptics 106' and a pair of movable haptics 106", it will be appreciated that any suitable number of attached haptics 106' and/or any suitable number of movable haptics 106" may be employed and remain within the scope of the present disclosure. Moreover, it will be appreciated that the haptics 106', 106" may be at any suitable angle relative to one another and are not limited to being spaced apart by 90° and/or 180°. Additionally, it will be appreciated that the haptics 106', 106" may extend from the ring 104 at any suitable angle.

Figure 9:
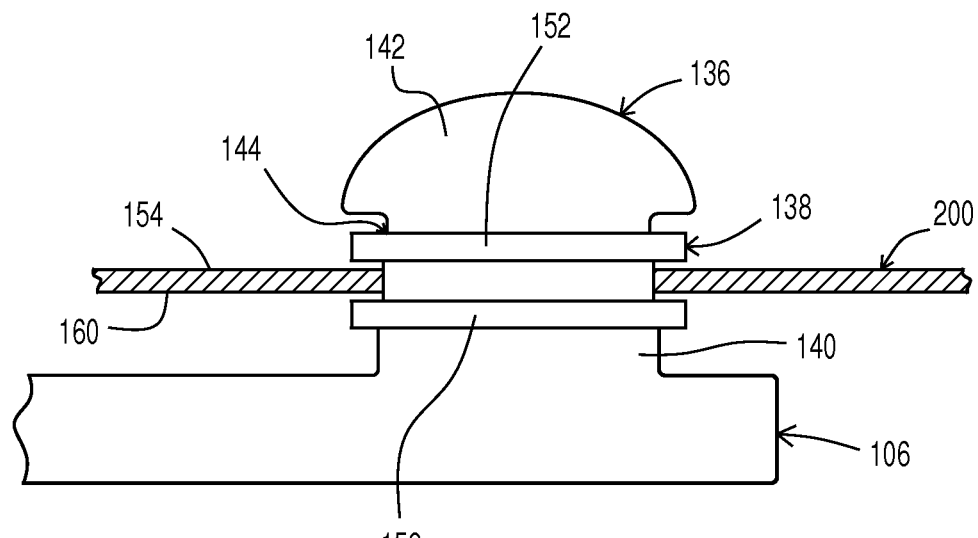
FIG. 9 is a side environmental view of a haptic protrusion and eyelet.

Referring again the FIGS. 1A and 1B, the distal ends of each haptic 106 may include any suitable implement for coupling each haptic 106 to the capsular bag 200. In the illustrative embodiment, each haptic 106 includes a protrusion 136 for engaging a corresponding eyelet 138 disposed in the capsular bag 200. As best shown in FIG. 9, the protrusion 136 may include a columnar member 140 extending from the haptic 106. The distal end of the columnar member 140 may include a knob portion 142 having a diameter greater than the columnar member 140 and the eyelet aperture 144 such that the haptic 106 may be lockingly coupled to the eyelet 138 once the protrusion 136 is inserted through the eyelet aperture 144. It will be appreciated that the protrusion 136 may extend from the haptic 106 at any suitable angle. While the illustrative embodiment employs a protrusion 136 having a columnar member 140 and a knob portion 142, it will be appreciated that the protrusion may have any suitable configuration capable of being lockingly coupled to a corresponding eyelet 138. For example, and without limitation, the protrusion may be a hook operable to engage a corresponding eyelet. Alternatively, each haptic 106 may include a fastener for directly engaging the capsular bag 200. For example, and without limitation, each haptic 106 may include a hook, a retractable extension, or the like for puncturing and securing attachment of the haptic 106 to the capsular bag. In yet another alternative, each haptic 106 may be secured to the capsular bag with a tissue adhesive or the like.

Each haptic 106 may be formed from any suitable material, including, but not limited to, acrylic, polymethyl methacrylate, any other suitable polymer, a metal, a composite, etc. The haptics 106 may also be formed from, or otherwise include, a light sensitive polymer, whereby the haptic 106 shrinks or expands when exposed to a specific wavelength of light, such that the shape and/or length of each haptic 106 may be adjusted post-operatively to provide for the adjustment of the refractive power of the optic 102. Also, as shown in the FIGS., the haptics 106 may be substantially straight, however, it will be appreciated that the haptics 106 may have any suitable shape or configuration and remain within the scope of the present disclosure.

Figure 10:
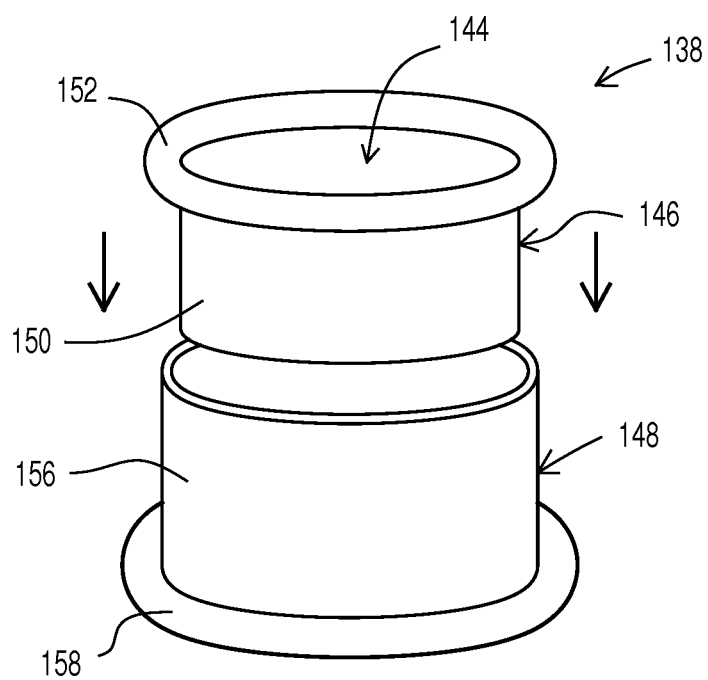
FIG. 10 is an exploded, perspective view of an illustrative eyelet.

Referring now to FIGS. 9 and 10, an illustrative, non-limiting and optional eyelet 138 is shown. Each eyelet 130 is configured to be coupled to a haptic 106 as well as provide reinforcement to the capsular bag 200. The eyelet 130 includes a first portion 146, a second portion 148 and an aperture 144. The first portion 146 includes an annular body 150 and lip 152 for abutting an exterior surface 154 of the capsular bag 200. The second portion 148 includes an annular body 156 and a lip 158 for abutting an interior surface 160 of the capsular bag 200. The first and second portions 146, 148 are configured to be coupled together such that a portion of the capsular bag 200 may be secured between the first portion lip 152 and second portion lip 158. In one embodiment, one of the first portion 146 and second portion 148 is telescopically received in the other of the first portion 146 and second portion 148 whereby the first and second portions 146, 148 are held together by a friction fit. Alternatively, the first and second portions 146, 148 may be coupled together via bonding, adhesives, fasteners, or the like. It will, however, be appreciated that the first and second portions 146, 148 may be coupled together via any suitable means and remain within the scope of the present disclosure. For example, and without limitation, one of the first and second portions 146, 148 may include a protrusion and the other of the first and second portion 146, 148 may include a slot or aperture for lockingly receiving said protrusion. The apertures of the first and second portions 146, 148 together form the eyelet aperture 144. The eyelet aperture 144 is configured to receive a haptic protrusion 136 such that a corresponding haptic 106 may be lockingly engaged to each eyelet 138 as previously discussed.

Referring now to FIGS. 1-10, a method for implantation of the intraocular lens 100 is also disclosed. The patient's natural lens is removed as is typically known in the art. Briefly, and without limitation, the patient's pupil is pharmacologically dilated. A hole 202, or capsulorhexis, is made in the anterior of the patient's caspular bag 200 and the natural lens is removed.

The intraocular lens 100 may then folded along a line 134 substantially parallel with the attached haptics 106' (see, e.g., FIG. 8A) and inserted through the capsulorhexis 202. The optic 102 may then be unfolded or otherwise allowed to unfold. If the optic 102 is configured to correct astigmatism, the lens 100 may be rotated to a predetermined orientation in the patient's eye by rotating the lens 100 such that the markings 111 on the optic 102 are properly positioned to allow for astigmatic correction by the optic 102.

If the lens 100 includes movable haptics 106", the movable haptics 106" may be moved to their respective permanent positions (see, e.g., FIG. 8B). The eyelets 138 may then be installed in the capsular bag 200 wherein the number of and position of the eyelets 138 corresponds to the number of haptic 106, 106', 106". Each haptic protrusion 136 may then coupled to a corresponding eyelet 138. In an alternative embodiment, the eyelets 138 may be installed prior to the lens 100 being inserted through the capsulorhexis 202.

In one embodiment, the lens 100 is smaller than the capsular bag 200 and the eyelets 138 are positioned such that the lens 100 may have to be "over-stretched" to couple the haptic protrusions 136 to corresponding eyelets 138 in the capsular bag 200. The terms "over-stretched" or "over-stretching," as used herein refer to stretching the lens 100 (or optic 102) beyond the maximum unaccommodated position under normal use by the patient after implantation. Over-stretching the lens 100 in this manner may allow for the lens 100 to recoil slightly after the protrusions 136 are coupled to the eyelets 138, and in some instances after the pharmacologically induced dilation begins to subside, whereby at least some slack in the capsule 200 is reduced and whereby restoration of at least some tension in the patient's zonules provided by the lens 100 may be further enhanced. Additionally, over-stretching the lens 100 during implantation may also ensure distance correction by the lens 100 after the pharmacologically induced dilation of the patient's eye subsides and the patient's eye returns to a more normal function, including a normal maximal dilation (i.e., not pharmacologically induced and which is frequently less than a pharmacologically induced dilation). Also, embodiments where the optic 102 rests in an accommodated state or where the optic 102 is biased to an accommodated state by the ring 104, the lens 100 may reduce the amount of work required from the ciliary muscle for accommodation. In an alternative embodiment, the lens 100 is sized larger than the capsular bag 200 such that the haptics 106, 106', 106" directly abut the ciliary muscle and forces generated from contraction and relaxation of the patient's ciliary muscle are received directly by the haptics.

In embodiments where the haptics 106, 106', 106" are capable of post-operative adjustment by exposure to specific wavelength(s) of light, once the lens 100 has been implanted, the power of the optic 102 may be adjusted by exposing the haptics to the specific wavelength(s) of light to adjust the lengths of said haptics and thereby adjust the power of the optic 102.

Referring now to FIGS. 11-31, another illustrative embodiment of a intraocular lens 300 is shown. The lens 300 is analogous in most respects to the lens 100 of FIGS. 1-10 and a correlation of parts is generally indicated in this embodiment by indexing the numerals in FIGS. 1-10 by 200. The intraocular lens 300 includes an adjustable optic 302, an elastic ring 304, and one or more haptics 306.

Figure 13:
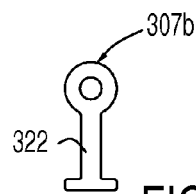
FIG. 13 is a top view of a fastener member.
Figure 14A:
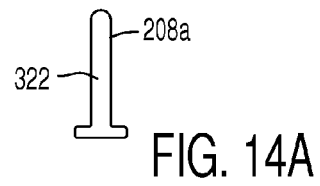
FIG. 14A is a top view of an alternative fastener member.
Figure 14B:
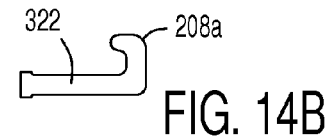
FIG. 14B is a side view of the fastener member of FIG. 14A.
Figure 14C:
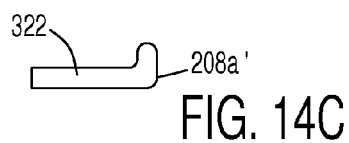
FIG. 14C is a side view of an alternative fastener member.

In the illustrative embodiment, the haptics 306 extend from the fastener member(s) 322 to a scaffold member 405. As shown in FIGS. 13 and 15A, the proximal end of each haptic 306 may include a hook portion 307a (FIG. 15A) that engages corresponding loop portion 307b of a fastener member 322 (FIG. 13). Alternatively, as shown in FIGS. 14A, 14B, 14C and 15B, the proximal end of each haptic 306 may include a loop portion 307b that engages a corresponding hook portion 208a, 208a' of a fastener member 322 (FIGS. 14A-14C) wherein the hook portion 208a may curl back towards the fastener member 322 (FIG. 14B) or may be substantially perpendicular to the fastener member 322 (FIG. 14C). Although a hook and loop mechanism is used herein to attach the ring scaffold/haptics to the optic, it is understood that other mating mechanisms will serve the same purpose of attachment and are considered within the scope of present disclosure, e.g. ball-and-socket, prong-and-receptacle, or any male/female complementary shape mating mechanism. Magnets may also be used to couple the optic to the haptic. In an alternative embodiment the fastener member 322 and elastic ring 304 may be formed of the same substance and form a single entity. The fastener member form a mechanism of attachment between the optic 302/elastic ring 304 complex to the surrounding ring scaffold 405/haptic 306 complex. The illustrative embodiment uses a hook 307a and loop 307b mechanism, however it is understood that any mating mechanism that can accomplish attachment between the scaffold 405/haptic 306 complex to the optic 302/elastic ring 304 complex may be considered part of present disclosure. These mechanisms include but are not limited to ball-and-socket, prong-and-receptacle, interlocking coils or magnets. The two mating ends may be alternatively placed on either the haptic 306, or the optic 302/elastic ring 304 complex.

The scaffold member 405 is configured to be coupled to the patient's capsular bag 200 as well as provide an anchoring structure for the haptics 306 whereby the optic 302 may be coupled to the capsular bag 200 wherein movement of the capsular bag 200 is imparted to the optic 302. The scaffold member 405 and the haptics 306 may be formed from any suitable biocompatible and resilient material, such as, but not limited to, polymethyl methacrylate (PMMA), acrylic, polyimide, or silicone. The ring scaffold member 405 and/or haptics 306 may include dark pigmentation so that either may absorb laser light, such as, but not limited to, Argon or YAG laser, for modification of shape after insertion. Modification of shape may be cutting the scaffold member 405 into segments, spot welding of the scaffold member 405 together, shortening or lengthening of haptics 306 to modify post-operative refractive power of AIOL, or any other suitable shape modification that helps to accomplish the purpose of AIOL. While the illustrative scaffold 405 is annular in shape, it will be appreciated that the scaffold may be any suitable shape and remain within the scope of the present disclosure.

The scaffold member 405 may include apertures for receiving hook portions at the distal end of the haptics. Alternatively, the scaffold member 405 may include hook portions to be received by loop portions at the distal end of each haptic. In yet another alternative, the haptics 306 may be integral with the scaffold member 405.

Figure 18:
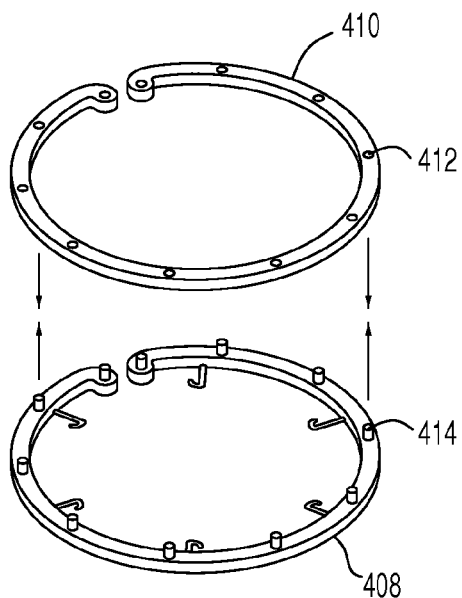
FIG. 18 is perspective view of an endocapsular portion of the ring scaffold and an extracapsular portion of the ring scaffold.
Figure 19:
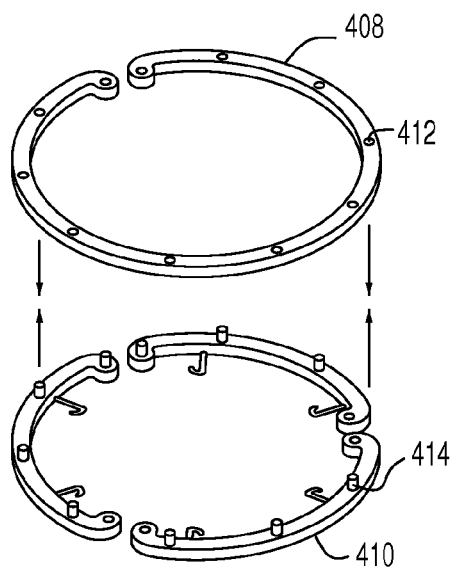
FIG. 19 is an alternative perspective view of an endocapsular portion of the ring scaffold and an extracapsular portion of the ring scaffold.
Figure 11A:
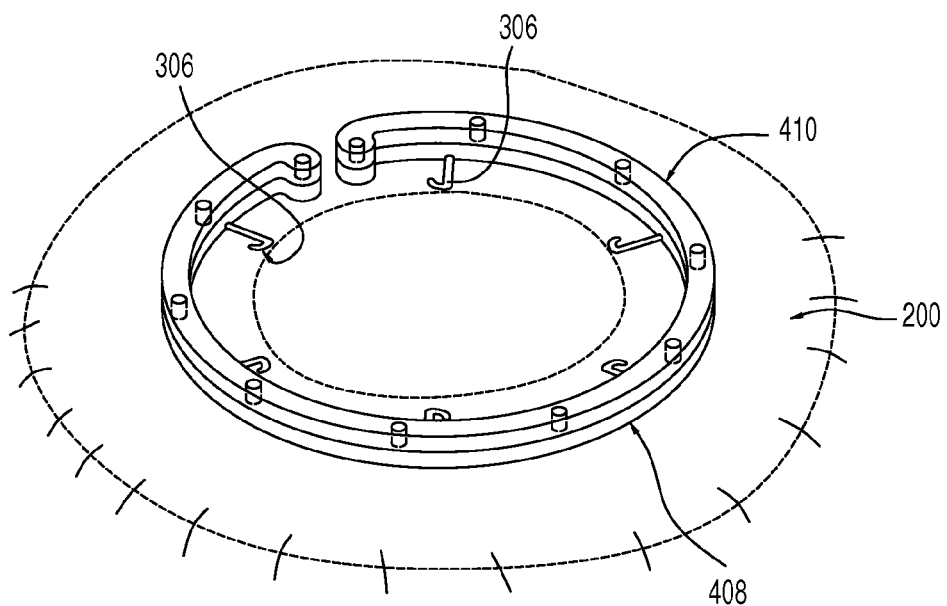
FIG. 11A is an environmental view of an alternative accommodating intraocular lens.
Figure 11B:
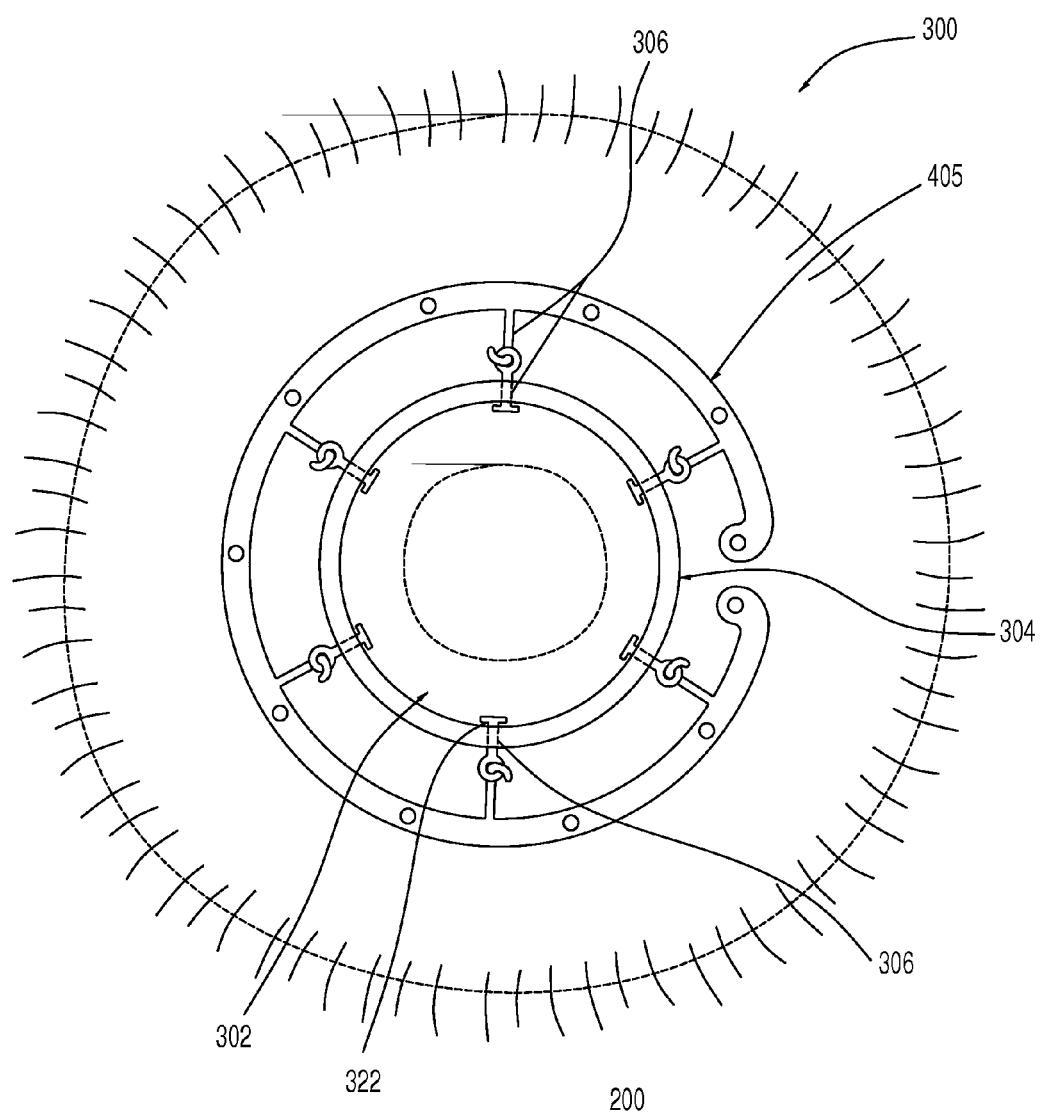
FIG. 11B is a top view of the accommodating intraocular lens of FIG. 11A.
Figure 12:
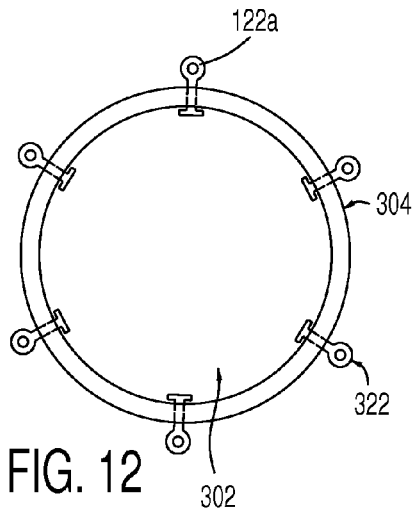
FIG. 12 is a top view of an optic and elastic ring.

The scaffold member 405 may comprise an endocapsular portion 408 and an extracapsular portion 410. The endocapsular portion 408 may lockingly engage the extracapsular portion 410 such that the patient's capsular bag 200 is positioned between the portions 408, 410 and such that the scaffold member 405 is securely coupled to the capsular bag 200. As shown in FIGS. 18 and 19, one of the endocapsular portion 408 and an extracapsular portion 410 may include one or more pins 414 to be lockingly received by corresponding apertures 412 in the other of the endocapsular portion 408 or extracapsular portion 410. Such pins 414 may or may not pierce the patient's capsular bag 200 when lockingly engaging the corresponding apertures 412.

In one alternative, as shown in FIG. 20, the endocapsular portion 408 may be formed from a plurality of endocapsular segments 408a, 408b, 408c. Likewise, as shown in FIG. 21, the extracapsular portion 410 may be formed from a plurality of extracapsular segments 410a, 410b, 401c. It will be appreciated that each of the endocapsular portion 408 and extracapsular portion 410 may be formed from any suitable number of segments. Also, it will be appreciated that one of the endocapsular portion 408 and extracapsular portion 410 may be formed from a plurality of segments and the other of the endocapsular portion 408 and extracapsular portion 410 may be a single piece or of a different number of segments. In an alternative embodiment, part or all of either endocapsular 408 or extracapsular ring scaffold 410 may take on coil shape. The coil shape would facilitate ring expansion/ contraction and also locking engagement between the endocapsular and extracapsular portions. It will also be appreciated that although ring scaffold and haptics are described separately, they are in fact connected to each other and may be considered a single entity, and that any future inventions that designate a haptic or ring scaffold with the same general shape without separate names would still be an infringement of present disclosure.

As shown in FIGS. 22-24, the endocapsular portion 408 may have any suitable configuration. For example, the endocapsular portion 408 may be substantially flat (FIG. 22). Alternatively, the endocapsular portion 408 may be undulating and have one or more mating points 416 (FIGS. 23-24). Similarly, as shown in FIGS. 25-27, the extracapsular portion 410 may have any suitable configuration. For example, the extracapsular portion 410 may be substantially flat (FIG. 25). Alternatively, the extracapsular portion 410 may be undulating and have one or more mating points 418 (FIGS. 26-27) whereby the extracapsular portion 410 and the endocapsular portion 408 may be engaged to each other about mating points 416 and 418 respectively during coupling to the capsular bag. It should be appreciated that any mating or locking arrangement between the endocapsular portion 408 and the extracapsular portion 410 can be used to hold the two portions together and still fall within the present disclosure. Such mechanisms may include tongue and groove or ball and socket mechanism and may be orientated radially or circumferentially about the portions. Magnets may also be used to couple the endocapsular 408 and extracapsular portions 410 of the scaffold rings.

In an alternative embodiment, as shown in FIGS. 28-31, the endocapsular portion 408 may be a singular piece having a first end 420 and a second end 422. The first end 420 may be lockingly engaged to the second end 422, typically after insertion into the patient's eye. Alternatively, the endocapsular portion 408 may be a continuous ring or made of a number of segments. In one embodiment, as shown in FIG. 29A, a ball 426 and socket 424 assembly is employed to lockingly secure the first end 424 to the second end 426. Alternatively, as shown in FIG. 29B, a hook 430 and loop 428 assembly may be employed to secure the first end 424 to the second end 426.

Figure 31:
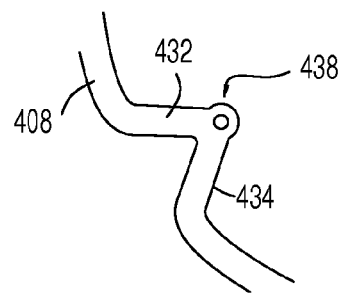
FIG. 31 is a top view of an alternative haptic.
Figure 30A:
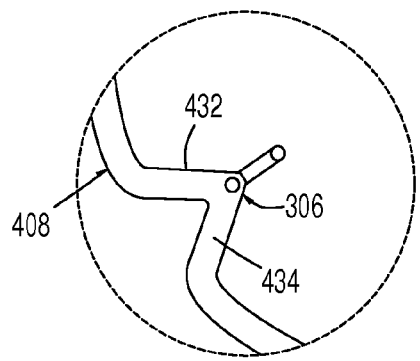
FIG. 30A is a top view of a haptic of the endocapsular portion of the ring scaffold of FIG. 28.
Figure 30B:
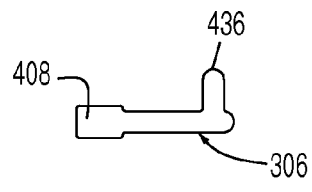
FIG. 30B is a side view of the haptic of FIG. 30A.

The endocapsular portion 408 of the scaffold may include a haptic 306 that includes a first arm 432 and second arm 434 that extend from the endocapsular portion 408. As shown in FIG. 30B, the distal end of the arms 432, 434 may converge at a hook portion 436 for engaging the elastic ring. Alternatively, as shown in FIG. 31, the distal ends of the arms 432, 434 may converge at a loop portion 438 for engaging the elastic ring directly or via an additional haptic linked to the elastic ring. While FIGS. 28-31 show an endocapsular portion 408, it will be appreciated that the extracapsular portion 410 may, or may not, be configured similarly. It should be appreciated that the point of convergence of arms 432 and 434 may have any number of structures to provide for the attachment to the elastic ring directly or via an additional haptic linked to the elastic ring and still be within the parameters of the present disclosure. While FIGS. 28-31 show an endocapsular portion 408, it will be appreciated that the extracapsular portion 410 may, or may not, be configured similarly. The structure, whereby the endocapsular portion 408 includes a first arm 432 and second arm 434, provides a "buckle point" that assists in the contraction and expansion of the scaffold in the horizontal plane. In an alternative embodiment, the haptics 306 may be integral with the extracapsular portion of the ring scaffold 410 instead of endocapsular portion 408.

Figure 11C:
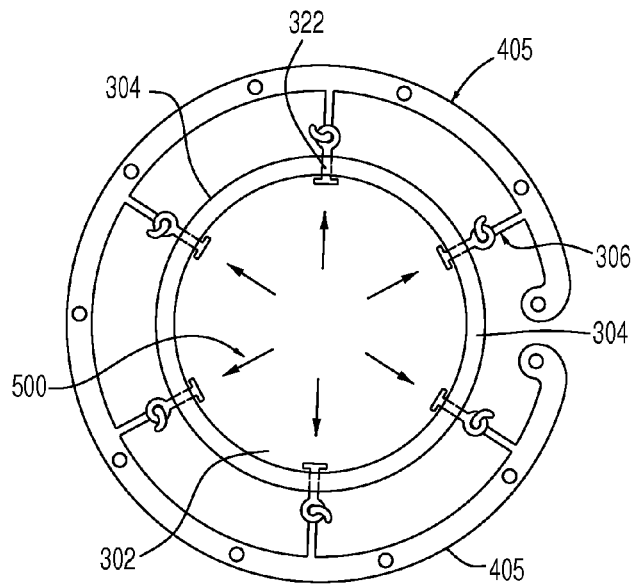
FIG. 11C is another top view of the accommodating intraocular lens of FIG. 11A.
Figure 29A:
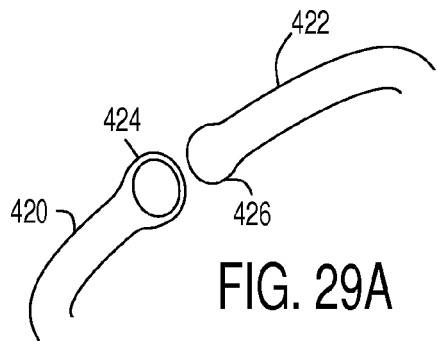
FIG. 29A is a side view of the ends of the endocapsular portion of the ring scaffold of FIG. 28.
Figure 29B:
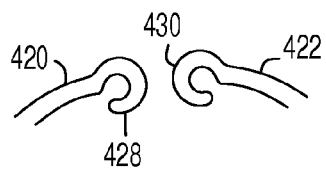
FIG. 29B is a side view of alternative ends of an endocapsular portion of the ring scaffold.
Figure 28:
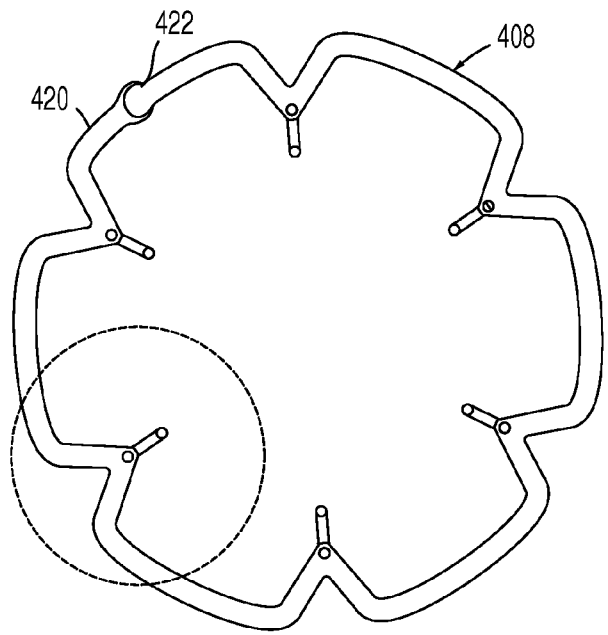
FIG. 28 is a top view of an alternative endocapsular portion of the ring scaffold.

The method for implanting the lens 300 is substantially similar to the lens 100 of FIGS. 1-10 with respect to the adjustable optic 302 and an elastic ring 304 except for the scaffold member 405 is installed first. The endocapsular portion 408 may be inserted via a small incision into the capsular bag. The extracapsular portion 410 may be inserted into the ciliary sulcus space anterior to the capsule. Optionally, the portions 408, 410 may be rotated to a predetermined position for astigmatic correction. The endocapsular portion 408 and extracapsular portion 410 may then be coupled to one another so as to capture a portion of the capsular bag therebetween. Once the optic 302 and ring 304 are inserted, the haptics 306 may be coupled to the distal end of the fastener member 304. As best shown in FIG. 11C, when the haptics 306 are coupled to the elastic ring 304, the optic 302 is stretched to the unaccommodated state (as represented by force vectors 500).

Likewise, as described above for the embodiments shown in FIGS. 1-10 where the haptics 106, 106', 106" are capable of post-operative adjustment by exposure to specific wavelength (s) of light, such post-operative adjustment is contemplated for the haptics 306. In this embodiment, the optic 302 is sized to fit easily within scaffold such that the optic 302 is not appreciably stretched when coupling the elastic ring to the haptics 306. However, once the optic is in attached to the scaffold, a laser or other light source can be used to alter the shape of the haptics 306, for example, shorten them and thereby stretch the optic 302 to the unaccommodated state. It is also possible to adjust the power of the optic 302 post-operatively by exposing the haptics 306 to the specific wavelength(s) of light to adjust the lengths of said haptics. While the present disclosure has been described in connection with what is considered the most practical and preferred embodiment, it is understood that this disclosure is not limited to the disclosed embodiments, but is intended to cover various arrangements included within the spirit and scope of the broadest interpretation so as to encompass all such modifications and equivalent arrangements. For example, although it has been described how a fully assembled AIOL, consisting of the haptics, ring, and optic is inserted into the eye in a pre-assembled form, it is within the scope of this invention and it is contemplated by the inventor, that the above listed components can be separately inserted into the eye and the AIOL assembled therein.

What is claimed is:

1. An intraocular lens comprising:
    an adjustable optic, the optic capable of being moved between an accommodated state and an unaccommodated state, the optic comprising:
        an anterior portion;
        a posterior portion;
        a sidewall between the anterior portion and the posterior portion;
    a ring disposed about the optic sidewall, further comprising a fastener member for coupling the ring to the optic sidewall; and
    a haptic capable of being coupled to the ring and a patient's capsular bag, further comprising a scaffold for coupling the haptic to the patient's capsular bag, wherein the scaffold is configured to be coupled to the patient's capsular bag, wherein the haptic is configured to be coupled to the scaffold, and wherein the scaffold comprises an endocapsular portion and an extracapsular portion wherein the endocapsular portion is configured to be coupled to the extracapsular portion such that a portion of the patient's capsular bag is positioned between the endocapsular portion and extracapsular portion.

2. The intraocular lens of claim 1 wherein at least one of the endocapsular portion and extracapsular portion comprise a plurality of segments.

* * * * *